(12) United States Patent
Foxman

(10) Patent No.: US 7,037,532 B2
(45) Date of Patent: May 2, 2006

(54) HANGOVER RELIEF COMPOSITION

(75) Inventor: Eric Foxman, Portland, OR (US)

(73) Assignee: Innovation Ventures, LLC, Walled Lake, MI (US)

( * ) Notice: Subject to any disclaimer, the term of this patent is extended or adjusted under 35 U.S.C. 154(b) by 199 days.

(21) Appl. No.: 10/792,333

(22) Filed: Mar. 3, 2004

(65) Prior Publication Data

US 2005/0196465 A1  Sep. 8, 2005

(51) Int. Cl.
*A61K 35/78* (2006.01)
(52) U.S. Cl. ..................................................... 424/725
(58) Field of Classification Search ................. 424/725
See application file for complete search history.

*Primary Examiner*—Michael Meller
(74) *Attorney, Agent, or Firm*—Chernoff, Vilhauer, McClung & Stenzel, LLP

(57) ABSTRACT

A homeopathic hangover relief composition is disclosed, the composition comprising a mixture of aqueous ethanolic tinctures of six or seven homeopathic ingredients.

10 Claims, No Drawings

HANGOVER RELIEF COMPOSITION

BACKGROUND OF THE INVENTION

Even when consumed in moderation, the ingestion of alcoholic beverages may lead to a variety of post-consumption symptoms, including headache, tremulousness, nausea, sour stomach, diarrhea, dizziness, fatigue and decreased cognitive or visual-spatial skills, collectively and popularly known as "hangover."

Such symptoms are believed to be connected to dehydration, hormonal alterations, deregulation of cytokine pathways and a variety of other toxic effects of alcohol. Of these, dehydration is believed to be one of the primary causes of hangover symptoms. As an alcoholic beverage is ingested, ethanol is absorbed into the blood stream. In the body, ethanol and its metabolites are identified as toxins and broken down to less harmful chemical entities. The liver and kidneys are the organs where most of the toxin processing takes place. In order for toxins to be processed adequately by the liver and kidneys, they must be dissolved in water. When the amount of toxins generated by alcohol consumption is higher than the amount of water available in the stomach, water is drawn from other areas of the body, such as the blood, the lymph nodes and the brain, causing dehydration, which in turn may result in effects ranging from mere headaches to serious harm to the brain, kidneys, liver, lymph nodes and other vital organs of the body, up to and including death.

Another toxic effect of alcohol consumption is associated with the buildup of acetaldehyde during the metabolism of ethanol by the liver and kidneys. Ethanol breakdown in the liver involves two steps which are catalyzed by two different enzymes. In the first step, the enzyme alcohol dehydrogenase converts ethanol in to acetaldehyde, which is toxic. In the second step, the enzyme dehydrogenease converts the acetaldehyde into harmless acetate. When acetaldehyde is produced at a faster rate than it is converted to acetate, excess acetaldehyde accumulates in the liver, causing severe toxic effects, up to and including breakdown of liver tissue.

Many attempts have been made to devise remedies to alleviate the many symptoms of hangover, but very few are effective against the large variety of symptoms noted above. In addition, many over-the-counter remedies have their own deleterious side effects. There is therefore a need for an inexpensive composition for broad spectrum relief from the many symptoms of hangover that is safe and effective. This need is fulfilled by the present invention, which is summarized and described in detail below.

BRIEF SUMMARY OF THE INVENTION

In a first aspect, the invention comprises a hangover relief composition comprising a mixture of aqueous ethanolic tinctures of six or seven active homeopathic ingredients, namely (i) *Cinchona oficinalis* ("*Cinchona*"), (ii) *Lobelia inflata* ("*Lobelia*"), (iii) *Nux vomica*, (iv) *Quercus glandium spiritus* ("*Quercus*"), (v) *Ranunculus bulbosus* ("*Ranunculus*"), and (vi) Zinc; and optionally (vii) *Rhododendron Crysanthum* ("*Rhododendron*"). Inclusion of ingredient (vii) renders the composition especially effective for relief from headaches caused by drinking wine.

In a second aspect, the invention comprises a method for the treatment of hangover symptoms in a human comprising administering an effective amount of the aforesaid composition.

DETAILED DESCRIPTION OF PREFERRED EMBODIMENTS

According to the present invention the composition is made by combining equal parts by weight of aqueous ethanolic tinctures of the aforementioned active homeopathic ingredients. Each ingredient is diluted in accordance with conventional homeopathic formulation procedures using an aqueous solution containing 20 vol % of 95 vol % ethanol.

Active ingredients (i)–(v) and (vii) are all commercially available in 20 vol % aqueous ethanolic solutions from Apotheca Naturale, Inc. of Woodbine, Iowa and are derived from plants as follows: (i) *Cinchona*—an alkaloid extracted from the bark of the *Cinchona* shrub or tree, containing at least 2.5 wt % quinine and at least 5 wt % total alkaloids; (ii) *Lobelia*—an alkaloid- and procain-containing extract from the entire *Lobelia* herb plant containing not less than 0.25 wt % total alkaloids; (iii) *Nux vomica*—the active ingredient extracted from coarsely powdered seeds of the Poison nut or Quaker buttons plant, containing at least 1.2 wt % and 1.5 wt % of the alkaloids strychnine and frucine, respectively; (iv) *Quercus*—the active ingredient extracted from the acorns of Common oak, containing not less than 25 wt % hydrolysable tannins; (vi) *Ranunculus*—the active ingredient extracted from the entire herb Buttercup or Bulbous crowfoot, containing at least 10 wt % total crude saponins; and (vii) *Rhododendron*—the active ingredient extracted from the leaves of the Golden Flowered *Rhododendron* plant. Active ingredient (vi) (Zinc) is an elemental metal and is commercially available in 20 vol % aqueous ethanolic tinctures of finely ground (325 mesh) metal from Apotheca Naturale.

In a preferred formulation, most of the active ingredients are diluted 12x in accordance with standard homeopathic dilution procedures, with one of the ingredients being diluted 6x and two diluted 30x. By "standard homeopathic dilution procedures" is meant that a dilution of 1x=1 part by weight active to 9 parts by weight diluent or, in other words, a 10 wt % solution; a 2x dilution=1 part by weight of a 1x solution to 9 parts by weight of diluent dilution, or a 1 wt % solution; a 3x dilution=1 part by weight of a 2x solution to 9 parts by weight of diluent, or a 0.1 wt % solution; and so on. All dilutions may vary with a tolerance of ±10%, preferably ±2%.

Ingredients (i)–(iii) and (v) are preferably diluted 12x, while ingredient (iv) is preferably diluted 6x and ingredients (vi) and (vii) are preferably diluted 30x. The solutions of actives may form from about 75 to about 95 wt % of the composition, preferably about 90 wt %.

While the composition may be formulated into a wide variety of administration forms such as drops or sprays, the most preferred form is by incorporating the composition into a coating, which is then coated onto an inactive core or prill to form a tablet, as this form imparts no bitter taste and has been shown to be effective at quick adsorption into the bloodstream. Any conventional pharmaceutical polymer used for coating may be used as the coating material, including ethyl cellulose, hydroxypropyl cellulose and hydroxypropyl methylcellulose (HPMC). An especially preferred coating formulation comprises HPMC and may include one or more dissolution enhancers such as polyethylene glycol and one or more inert excipients. Preferred inert excipients, from which the core may also be made, include whey, sucrose, microcrystalline cellulose, carnauba wax, calcium carbonate, carbon, sucrose, stearic acid, croscarmellose sodium, magnesium stearate, titanium dioxide, and silicon dioxide. The following Example demonstrates how to formulate an exemplary embodiment of the invention.

EXAMPLE

The composition of the present invention, comprising a liquid mixture of the six active ingredients, was formulated as follows. The mixture of active ingredients comprised six equal parts by weight of ethanol/water solutions made from 20 vol % aqueous ethanolic tinctures of the six active ingredients noted above from the commercially available source mentioned above. Ingredients (i)–(iii) and (v) (*Cinchona, Lobelia, Nux Vomica* and *Ranunculus*) were diluted with a mixture of 20 vol % of 95 vol % ethanol in distilled water to form a $10^{-10}$ wt % or 12x solution in accordance with the procedures set forth in the *U.S. Homeopathic Pharmacopeia* (1999) at pages 39–41. Ingredient (iv) (*Quercus*) was diluted in the same manner to form a $10^{-4}$ wt % or 6x solution. Ingredient (vi) (325 mesh Zinc powder) was diluted in the same manner to form a $10^{-28}$ wt % or 30x solution. All six diluted solutions of actives were then combined in a mixing vessel and thoroughly mixed with a magnetic stirrer for about 15 minutes to form a homogeneous liquid mixture.

Tablet cores containing 1.3 g inactive ingredients were formed by mixing the excipients noted and compressing them in a tablet press with 15 kiloPonds pressure. The excipients and their amounts were microcrystalline cellulose (670 mg); calcium carbonate (308 mg); carbon (172 mg); sucrose (100 mg); stearic acid (30 mg); croscarmellose sodium (10 mg); and magnesium stearate (10 mg).

The liquid mixture of six active ingredients was then combined with approximately 54 wt % HPMC, 20 wt % polyethylene glycol, 20 wt % titanium dioxide and 3 wt % of a mixture of FD&C Yellow #6 and Red #40 as a colorant and thoroughly mixed to form a coating containing 16 wt % active ingredients. The coating was then coated onto the cores in a pan coater to yield tablets containing 4.6 wt % of the coating which contained 0.7 wt % active ingredients.

As a control, a group of human subjects was administered placebo tablets (comprising a sucrose core with the same coating as in the Example above, but with no active ingredients) during consumption of a first alcoholic beverage at 8 p.m. Over the course of the next three hours the subjects consumed four to six additional alcoholic beverages. All reported substantial typical hangover symptoms the next morning.

A week later the tablets of the Example above were administered to the same group of subjects during consumption of a first alcoholic beverage at 8 p.m. Over the course of the next three hours the subjects consumed four to six additional alcoholic beverages. The next morning all subjects had either no hangover symptoms or minimal fatigue.

The terms and expressions which have been employed in the forgoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A composition for the relief of hangover symptoms comprising a mixture of aqueous ethanolic tinctures of the following ingredients:
   (i) *Cinchona oficinalis;*
   (ii) *Lobelia inflata;*
   (iii) *Nux vomica;*
   (iv) *Ranunculus bulbosus;*
   (v) *Quercus glandium spiritus;* and
   (vi) Zinc.

2. The composition of claim 1 further comprising an aqueous ethanolic tincture of *Rhododendron Crysanthum.*

3. The composition of claim 1 or 2 further comprising an inert excipient.

4. The composition of claim 3 wherein said inert excipient is selected from the group consisting of whey, sucrose, calcium carbonate, microcrystalline cellulose, carbon, carnauba wax, croscarmellose sodium, stearic acid, magnesium stearate and silicon dioxide.

5. The composition of claim 4 in the form of a coating coated onto a core.

6. The composition of claim 5 wherein said coating is selected from the group consisting of ethyl cellulose and hydroxypropyl methylcellulose.

7. A method of treating hangover symptoms in a human comprising the administration of an effective amount of a mixture of aqueous ethanolic tinctures of the following ingredients:
   (i) *Cinchona oficinalis;*
   (ii) *Lobelia inflata;*
   (iii) *Nux vomica;*
   (iv) *Rananculus bulbosus;*
   (v) *Quercus glandium spiritus;* and
   (vi) Zinc.

8. The method of claim 7 wherein said mixture further comprises an effective amount of an aqueous ethanolic tincture of *Rhododendron Crysanthum.*

9. The method of claim 7 or 8 wherein said administration is accomplished by the delivery of said composition in the form of a tablet.

10. The method of claim 9 wherein said tablet is in the form of said mixture coated onto a core.

* * * * *